(12) United States Patent
Scharnweber et al.

(10) Patent No.: US 8,043,627 B2
(45) Date of Patent: Oct. 25, 2011

(54) OSTEOGENIC COMPOSITE MATRIX, METHOD FOR THE PRODUCTION THEREOF AND IMPLANT AND SCAFFOLD FOR TISSUE ENGINEERING PROVIDED WITH A COATING FORMED BY SAID OSTEOGENIC COMPOSITE MATRIX

(75) Inventors: Dieter Scharnweber, Dresden (DE); Hartmut Worch, Dresden (DE); Susanne Bierbaum, Dresden (DE)

(73) Assignee: Nexilis AG, Grenchen (CH)

( * ) Notice: Subject to any disclaimer, the term of this patent is extended or adjusted under 35 U.S.C. 154(b) by 64 days.

(21) Appl. No.: 12/572,884

(22) Filed: Oct. 2, 2009

(65) Prior Publication Data

US 2010/0119575 A1    May 13, 2010

Related U.S. Application Data

(63) Continuation of application No. 11/578,607, filed as application No. PCT/DE2005/00728 on Apr. 15, 2005, now abandoned.

(30) Foreign Application Priority Data

Apr. 15, 2004   (DE) .......................... 10 2004 018 959

(51) Int. Cl.
*A61K 9/00* (2006.01)
*C07K 14/78* (2006.01)

(52) U.S. Cl. ....... 424/423; 424/484; 435/402; 427/2.26; 530/356

(58) Field of Classification Search .................. 424/422, 424/484, 423; 530/356; 435/402; 427/2.26
See application file for complete search history.

(56) References Cited

U.S. PATENT DOCUMENTS

| | | | |
|---|---|---|---|
| 4,448,718 | A | 5/1984 | Yannas et al. |
| 4,544,516 | A | 10/1985 | Hughes et al. |
| 5,116,389 | A | 5/1992 | Mitz et al. |
| 5,550,188 | A | 8/1996 | Rhee et al. |
| 2002/0090725 | A1 | 7/2002 | Simpson et al. |
| 2003/0141618 | A1 | 7/2003 | Braithwaite et al. |

FOREIGN PATENT DOCUMENTS

| | | |
|---|---|---|
| CA | 1087610 | 10/1980 |
| DE | 26 31 908 C2 | 2/1977 |
| DE | 691 15 934 T2 | 5/1996 |
| DE | 600 02 744 T2 | 4/2004 |
| EP | 0 608 211 B1 | 12/1995 |
| EP | 1 088 564 A1 | 4/2001 |
| EP | 1 312 383 A2 | 5/2003 |
| WO | 91/18 558 A1 | 12/1991 |

*Primary Examiner* — Chih-Min Kam
(74) *Attorney, Agent, or Firm* — Sughrue Mion, PLLC

(57) ABSTRACT

The invention relates to an osteogenic composite matrix consisting of collagen and non-collagen components of an extracellular matrix (ECM-components), to a method for producing said matrix, to a method for producing an implant or a scaffold for tissue engineering which is provided with a coating formed by said osteogenic composite matrix and is used for stimulating and accelerating a hard tissue formation such as, for example. The implant osseointegration in bones. The inventive osteogenic composite matrix comprises a collagen and at least one non-collagen ECM component or the derivatives thereof, wherein the collagen component consists of non-crosslinked collagen fibers produced by fibrillogenesis and the non-collagen ECM component or the derivatives thereof are integrated into said collagen fibers.

17 Claims, 7 Drawing Sheets

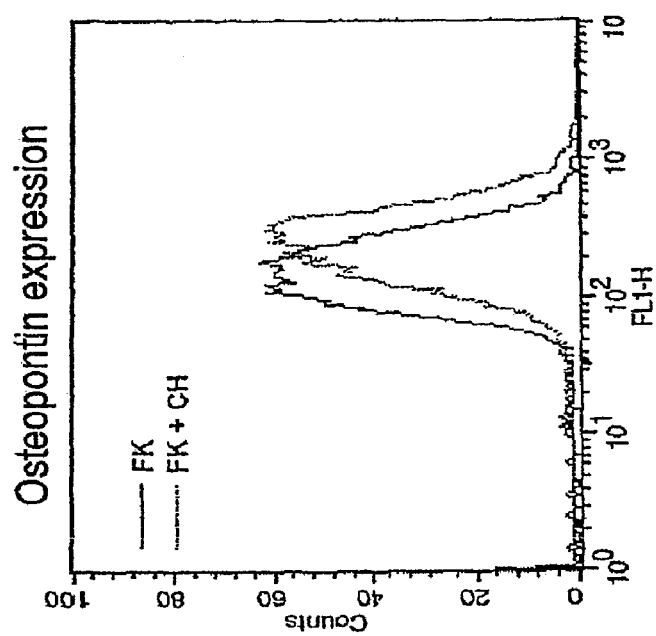
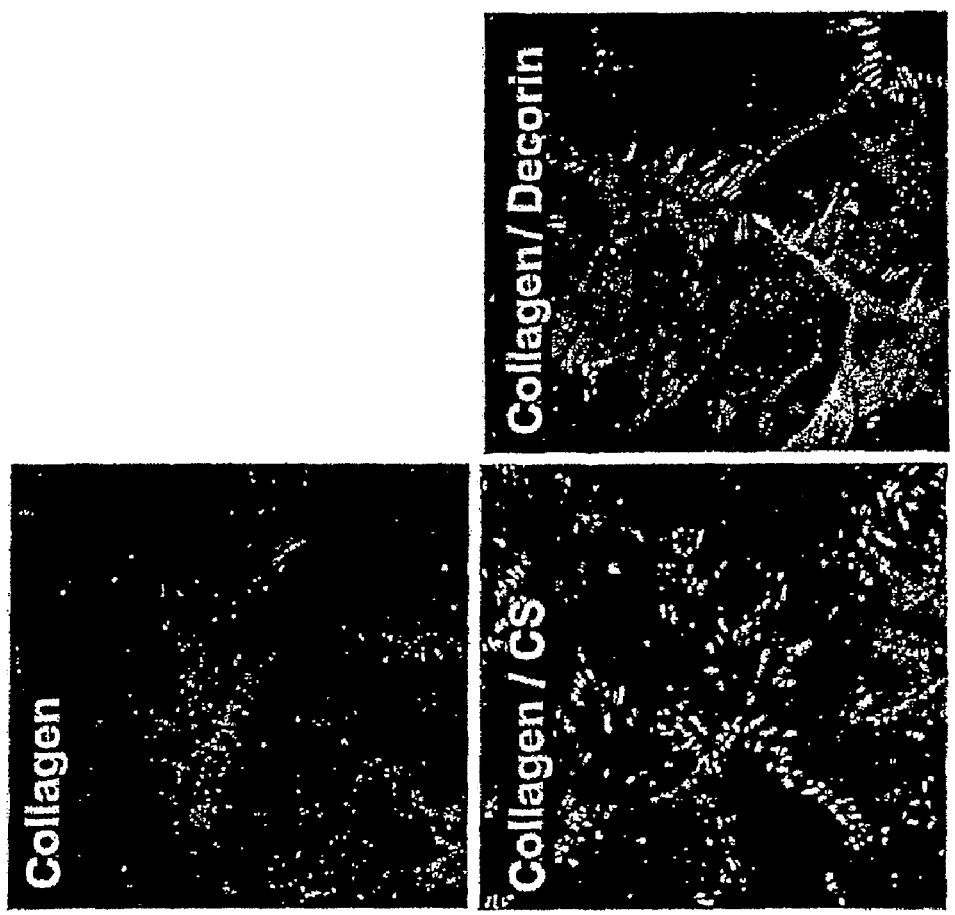
Fig. 5

OSTEOGENIC COMPOSITE MATRIX, METHOD FOR THE PRODUCTION THEREOF AND IMPLANT AND SCAFFOLD FOR TISSUE ENGINEERING PROVIDED WITH A COATING FORMED BY SAID OSTEOGENIC COMPOSITE MATRIX

This is a Continuation of application Ser. No. 11/578,607 filed May 30, 2007, now abandoned, which is a §371 application of PCT/DE2005/00728, filed Apr. 15, 2005, the disclosures of which are incorporated in their entirety.

TECHNICAL FIELD

The invention relates to an osteogenic matrix composite of collagen and noncollagenic components of the extracellular matrix (ECM components), a method for its production, a method for the production of an implant or of a scaffold for tissue engineering having a coating of an osteogenic matrix composite, and implants and scaffolds for tissue engineering having a coating of the osteogenic matrix composite for the stimulation and accelerated formation of hard tissue, such as, for example, in the field of osseointegration of implants into bone.

BACKGROUND ART

In the tissue, the cells are embedded in the native extracellular matrix (ECM), which is an important part of the cellular environment. The native ECM is a highly ordered, tissue-specific network which consists of collagens, glycoproteins, proteoglycans and glycosaminoglycans (GAG). The composition for various tissue and for various stages of development is very different here, such that the respective matrix has specific properties with respect to interaction with cells and growth factors.

The main structural protein of the native bone matrix is collagen type I, but various other matrix proteins such as proteoglycans and glycoproteins can interact with the collagen and influence the structure and function of the matrix. These noncollagenic ECM proteins fulfill specific functions in the matrix. Thus fibronectin, in addition to cell-binding properties, also has collagen- and GAG-binding properties [Stamatoglou and Keller, 1984, Biochim Biophys Acta. Oct 28; 719(1): 90-7], whereas small leucine-rich proteins (SLRPs) such as decorin not only play a role in the organization of the native ECM (decorin modulates fibrilogenesis in vivo), but also bind growth factors such as TGF-β or even play a role as signal molecules [Kresse and Schönherr, 2001, J Cell Phys 189: 266-274].

Proteoglycans and glycoproteins differ by their degree of glycosylation, the sugar content of the particularly highly glycosylated proteoglycans consisting of various glycosaminoglycans. The distribution of these chains can be tissue-specific, as, for example, for decorin (chondroitin sulfate in the bone, dermatan sulfate in the skin). The glycosaminoglycans are large, unbranched polysaccharides which consist of repeating disaccharides, which are composed, for example, of N-acetyl-galactosamine, N-acetylglucosamine, glucuronate or iduronate, which are sulfated to different degrees. The sugar chains are present in vivo bound to the proteoglycans and play an important role in the function of these proteins, i.e. in growth factor binding and modulation [Bernfield et al, 1999, Annu Rev Biochem, 68: 729-777].

Individual ECM constituents, in particular collagen, are already utilized for the biocompatible modification of scaffolds and implants in order to improve cell adhesion and tissue integration. In addition to collagen, further ECM components such as polysaccharides are used in various applications. Thus bone tissue was crosslinked with glycosaminoglycans in order to produce a three-dimensional scaffold for applications in tissue culture (WO 01/02030A2).

A chondroitin sulfate-containing mixture is used for the repair of bone defects; this promotes the healing of the connective tissue, mainly on account of the content of aminosugars and increased matrix production caused thereby (WO 98/27988, WO 99/39757). In combination with collagen, plant polysaccharides are used as wound coverings (EP 0140569 A2), and a combination of chitosan and GAGs is described as an agent for the stimulation of the regeneration of hard tissue (WO 96/02259). Collagen-GAG mixtures are produced here by acid coprecipitation, an unstructured precipitate and no defined collagen fibrils comparable to those in the native ECM being formed (U.S. Pat. Nos. 4,448,718, 5,716,411, 6,340,369).

With progressive availability of recombinant growth factors, those osteoinductive factors which actively influence the interactions between implants and surrounding tissue are increasingly of interest for implant applications [Anselme K (2000). Biomaterials 21, 667-68]. In connection with bone healing, the 'bone morphogenetic proteins' (BMP 2, 4-7) are particularly interesting since they induce the differentiation of mesenchymal stem cells in chondrocytes and osteoblasts and the formation of new bone [Celeste A J, Taylor R, Yamaji N, Wang J, Ross J, Wozney J M (1994) J. Cell Biochem. 16F, 100; Wozney J M, Rosen (1993). Bone morphogenetic proteins in Mundy, G R, Martin T J (Ed.) Physiology and pharmacology off bone. Handbook of experimental pharmacology, Vol. 107. Springer Verlag, Berlin, 725-748]. On account of these strong bone-inducing effects, recombinant BMPs are employed in various carrier materials in order to promote and to improve the regeneration of bone. Effective carriers for morphogenetic proteins should bind these, protect against hydrolysis, make possible subsequent, controlled release and promote the associated cell reactions. Moreover, such carriers should be biocompatible and biodegradable. Preferred carrier materials for BMPs are, for example, xenogenic bone matrix (WO 99/39757) or natural tissue subsequently crosslinked with GAGs (WO 01/02030 A2), or HAP, collagen, TCP, methylcellulose, PLA, PGA, and various copolymers (EP 0309241 A2, DE 19890329, EP 0309241 A2, DE 19890906, WO 8904646 A1, DE 19890601). Further applications comprise a crosslinked synthetic polymer which can contain additional components such as GAGs, collagen or bioactive factors (WO 97/22371), or crosslinked collagen mixed with glycosaminoglycans and osteogenic factors (WO 91/18558, WO 97/21447). The collagen-GAG mixture is in this case likewise produced by acid coprecipitation.

The use of recombinant growth factors is associated with great disadvantages. Since the recombinant factors usually have a lower activity than the endogenous factors occurring naturally in the tissue, in order to achieve an effect in vivo unphysiologically high doses are necessary. The administration of recombinant factors can only simulate the action of endogenous factors very incompletely.

By the use of factors which promote the action of the BMPs (Bone morphogenetic protein), or by the use of cells which can express the growth factors in situ, it is attempted to minimize or to circumvent this problem (WO 97/21447, WO 98/25460). Further problems can result from the fact that receptors for BMP occur in many different tissues; the function of these growth factors is thus not limited to the bone.

SUMMARY OF THE INVENTION

It is the object of the present invention to specify a biocompatible and biodegradable matrix composite which promotes and accelerates bone accumulation and bone growth in the immediate environment and on the surface of implants coated with the matrix composite, and which can be used in particular for the coating of synthetic, metallic or ceramic implants. A further aim of the invention is a coating of carrier materials (scaffolds) for tissue engineering, which assists the production of hard tissue in vitro and subsequently in vivo.

The invention is based on the scientific observation that for implants in contact with the bone in most cases an adequate amount of endogenous bone-forming factors is present on account of the surrounding tissue and the blood circulation. The bone-inducing effect of the BMPs, which can be observed under physiological conditions in vivo, is in all probability also not due to an individual, growth factor type, but the result of the synergistic action of a large number of endogenous factors.

Against this background, an implant coating is desirable which advantageously utilizes the endogenous bone-forming factors which are present at the implantation site.

According to the invention, the object is achieved by an osteogenic matrix composite of collagen and at least one noncollagenic ECM component or its derivatives, in which the collagen component consists of non-crosslinked collagen fibrils produced by means of fibrillogenesis, into which are integrated the at least one noncollagenic ECM component or its derivatives.

For the osteogenic matrix composite, according to the invention constituents of the extracellular matrix are used which are as similar as possible in composition and morphology to the matrix constituents which occur naturally in the bone, which are biocompatible and biodegradable, and have bone tissue-specific functions both in the binding and presentation of growth factors, and can directly influence the reactions of the cells. As a result, a microenvironment which is as approximate as possible to the in vivo conditions is presented to the cells, which positively influences the cell functions and the reaction to bone-forming factors such as growth factors.

The term collagen comprises all fibril-forming collagen types. Any collagen source is suitable which produces non-crosslinked, acid-soluble collagen monomers, recombinant or tissue derived, with and without telopeptides.

The term noncollagenic ECM components comprises both glycosaminoglycans and noncollagenic proteins, which are known constituents of the native ECM.

The term noncollagenic proteins comprises all matrix proteins having noncollagenic (proteoglycans and glycoproteins) or partly collagenic (FACITs) structure.

The main constituent of the osteogenic matrix composite is collagen of type I, II, III, V, IX, XI, or combinations thereof. In principle, every fibril-forming collagen type can be used which produces noncrosslinked, acid-soluble collagen monomers, collagen I, III and V being preferred, since these are the collagens mainly represented in the bone.

As GAG components, the osteogenic matrix composition contains chondroitin sulfate A, C, D, E; dermatan sulfate, keratan sulfate, heparan sulfate, heparin, hyaluronic acid or their derivatives, both individually and mixed, chondroitin sulfate being preferred. The sugars used are either prepared synthetically or isolated from biological sources.

As further noncollagenic matrix proteins, the osteogenic matrix composition can contain fibronectin, decorin, biglycan, laminin or versican, both individually and mixed, decorin and biglycan being preferred. The proteins used are either prepared recombinantly or isolated from biological sources in native form.

In order to generate a matrix which is as bone-analogous as possible, preferably collagen type I, decorin and biglycan and/or their GAG chains such as chondroitin sulfate are employed. Decorin or biglycan are used here in order to utilize bonds or synergisms between matrix, growth factor and cell. A further possibility, which is given preference here, is the use of GAG chains, which bind endogenous growth factors or can potentiate in their action; in particular the chondroitin sulfate frequently occurring in the bone. By combination of collagen with further GAGS or matrix constituents, further endogenous growth factors can also be used for accelerated healing, such as, for example, VEGF by heparan sulfate for the promotion of invascularization.

According to the invention, an osteogenic matrix composite of collagen and at least one noncollagenic ECM component or its derivatives is prepared such that collagen fibrils are produced by means of fibrillogenesis and that prior to fibrillogenesis at least one noncollagenic ECM component or its derivatives is added.

The collagen fibrils produced in this way can be utilized as a coating solution after resuspension in water or in a buffer system or lyophilized.

The fibrillogenesis (i.e. the formation of collagen fibrils) proceeds under the following conditions: temperature range from 4° C. to 40° C., preferably 25° C. to 37° C., collagen concentration of 50 to 5.000 μg/ml, preferably 250 to 1000 μg/ml, pH 4 to pH 9, preferably pH 6 to pH 8, phosphate content up to 500 mmol/l, preferably 30 to 60 mmol/l, NaCl content up to 1000 mmol/l, preferably up to 300 mmol/l.

By means of the preparation method according to the invention, an osteogenic matrix composite is formed having a defined structure and composition comparable to the situation in the native ECM.

An ordered, mutually transposed lateral association of the collagen monomers is characteristic of collagen fibrils in vivo, a typical band pattern having a periodicity of 64 to 67 nm resulting. This association is due, inter alia, to the charge pattern of the monomers. Fibril formation in vitro is induced by the pH, the temperature and the ionic strength of a cold, acidic collagen solution being brought to values in the vicinity of the physiological parameters.

Glycosaminoglycans or other matrix components are added to the solution containing collagen monomers before fibrillogenesis and thereby included in the following process of fibrillogenesis. Owing to the presence of the noncollagenic ECM components during the fibrillogenesis, these are integrated into the resulting fibril and a matrix is formed which corresponds to the native ECM with respect to the components used, the composition and structure.

During fibrillogenesis in vitro, collagen forms the characteristic transversely striated fibrils analogously to the in vivo structures, the structure of the resulting fibrils being influenced by the process parameters (pH, ionic strength, phosphate concentration) and by the nature and amount of the noncollagenic components present in the reaction solution. For in vivo matrix-modifying proteoglycans such as decorin, the greatest possible approximation to the native biological function is obtained in this way, as they can in this way also influence the structure of the resulting fibrils under in vitro conditions.

In contrast to structure formation, as a result of aggregation by fibrillogenesis collagen aggregation can also be induced by the addition of a polyanion, as the glycosaminoglycans represent, in the acidic medium, the electrostatic interactions existing between the GAG and the collagen monomer being causal. In such an acid precipitate, the association of the collagen monomers cannot be compared with that under approximately physiological conditions. Either an amorphous precipitate is formed or, with appropriate quantitative ratios and sufficient agreement of the charge patterns, a polymorphous aggregate such as segment long-spacing crystallites is formed.

For glycoproteins or proteoglycans such as decorin, there is no possibility of precipitation from the acidic medium.

In order to remain as close as possible to the conditions in vivo, according to the invention the collagen fibrils are not crosslinked. Although crosslinking would increase the stability, it would disadvantageously have an effect on those domains which can enter into specific bonds with endogenous bone-forming factors. This is in particular of importance for the function of the GAGs, since their growth factor-binding properties are based on free mobility of the sugar chain, which is restricted by the crosslinking. At the same time, the sugars can thus be released from the matrix, which is of importance for the presentation of the growth factors to the cell surface.

The invention comprises the use of the osteogenic matrix composite according to the invention for the coating of implants or scaffolds for tissue engineering.

Implants in the sense of the invention is understood as meaning all metallic, ceramic and polymeric implants or implants composed of various groups of materials whose surfaces are at least partly in contact with bone tissue. Likewise all metallic, ceramic and polymeric structures or structures composed of various groups of materials which serve as a scaffold for the tissue engineering of hard tissue.

The previously described osteogenic matrix composite is suitable, in particular, for the coating of nondegradable implants in bone contact, such as artificial hip joints, tooth implants or other load-bearing applications for which a rapid and solid integration of the implant into the bone is necessary.

The osteogenic matrix in combination with a three-dimensional, degradable implant, which is implanted as a bone replacement, can advantageously accelerate the integration and the reconstruction of the implant and also the new bone formation. These implants can contain, for example, particulate or three-dimensional structures consisting of calcium phosphates, but also polymeric materials, as a basic component.

For tissue engineering, the osteogenic matrix composition in combination with a scaffold can be advantageous for proliferation and differentiation of the bone-forming cells. As a scaffold, all three-dimensional, porous structures of synthetic and/or natural polymers (e.g. collagen), ceramic or metal individually or in combination are possible, biodegradable scaffolds of polymer and/or ceramic being given preference.

By means of the osteogenic matrix composite, bone-forming factors, such as, for example, growth factors which are present in vivo, are bound to the surface of the implant after implantation and their activity is increased. Advantageously, different endogenous factors which are present at the implantation site are recruited by the implant coated with the osteogenic matrix composite.

For the production of an implant or of a scaffold for tissue engineering, the coating solution comprising the osteogenic matrix composite is utilized in order to immobilize the osteogenic matrix composite on its surface advantageously by means of a dip-coating process. The collagen concentration of the coating solution can be between 0.5 mg/ml to 5 mg/ml, 1 mg/ml to 2 mg/ml being the preferred range. The osteogenic matrix composite is immobilized by incubation of the implant at room temperature for 5 to 20 minutes, subsequently dried and washed with water. The thickness of the resulting layer can be influenced by the concentration of the coating solution and by the number of process repetitions.

For the generation of a coated three-dimensional scaffold in combination with the described osteogenic matrix composite, the component mixture is advantageously introduced into the scaffold, which can be of metallic, ceramic and/or polymeric origin, prior to the beginning of fibrillogenesis. The fibrillogenesis is subsequently induced by increasing the temperature. The fibrils formed in situ can either remain as a collagen gel, or be dried analogously to the surface coating.

The implant or scaffold prepared in this way can advantageously be sterilized using the known nonthermal methods such as ethylene oxide or gamma irradiation and stored at room temperature.

The implant or scaffold coated according to the invention with an osteogenic matrix composite is delineated by the following advantages from the solutions known from the prior art:
  Good biological compatibility and functionality of the matrix produced by means of largely physiological composition and structure on account of the conditions in the production and use of components which correspond to those of the natural cell environment
  High variability with respect to employable components and their proportions in the component mixture
  Easy storage and sterilization conditions
  High specificity and efficiency due to the utilization of endogenous osteogenic factors.

BRIEF DESCRIPTION OF THE DRAWINGS

The invention is illustrated in more detail by means of the following working examples, comparative tests and figures.

The figures show

FIG. 5 Behavior of primary rat calvaria osteoblasts on various osteogenic matrix composites according to the invention — influence on adhesion and osteopontin expression FIG. 6 Activity of alkaline phosphatase in rat calvaria cells on various osteogenic matrix composites according to the invention after addition of 4 pmol/cm$^2$ of BMP-4

DETAILED DESCRIPTION OF THE INVENTION

Working Example 1

Fibril Structure After Fibrillogenesis Under Various Conditions

For the generation of the osteogenic matrix composite, a solution of collagen monomers in 0.01 M acetic acid is prepared by stirring for 24 hours at 4° C. The collagen fibrils are subsequently formed in the presence of the noncollagenic components by a process of self-aggregation (fibrillogenesis) in aqueous phosphate buffer solutions at neutral pH and a temperature of 37° C.

The range for the formation of the fibrils is between 0.5 and 5 mg of collagen/ml and 0.1 to 5 mg of glycosaminoglycan/ml, 1 mg/ml of collagen and 0.2 mg/ml of GAG and 30 μg/ml of proteoglycan being the preferred conditions. The preferred fibrillogenesis parameters were a 30 mmol/l phosphate buffer pH 7.0, either with 135 mmol/l of NaCl or without NaCl addition.

Glycosaminoglycans or other matrix components are added to the collagen monomers before fibrillogenesis and thereby integrated at least partially into the resulting fibrils in the following process of fibrillogenesis.

Figure 1:
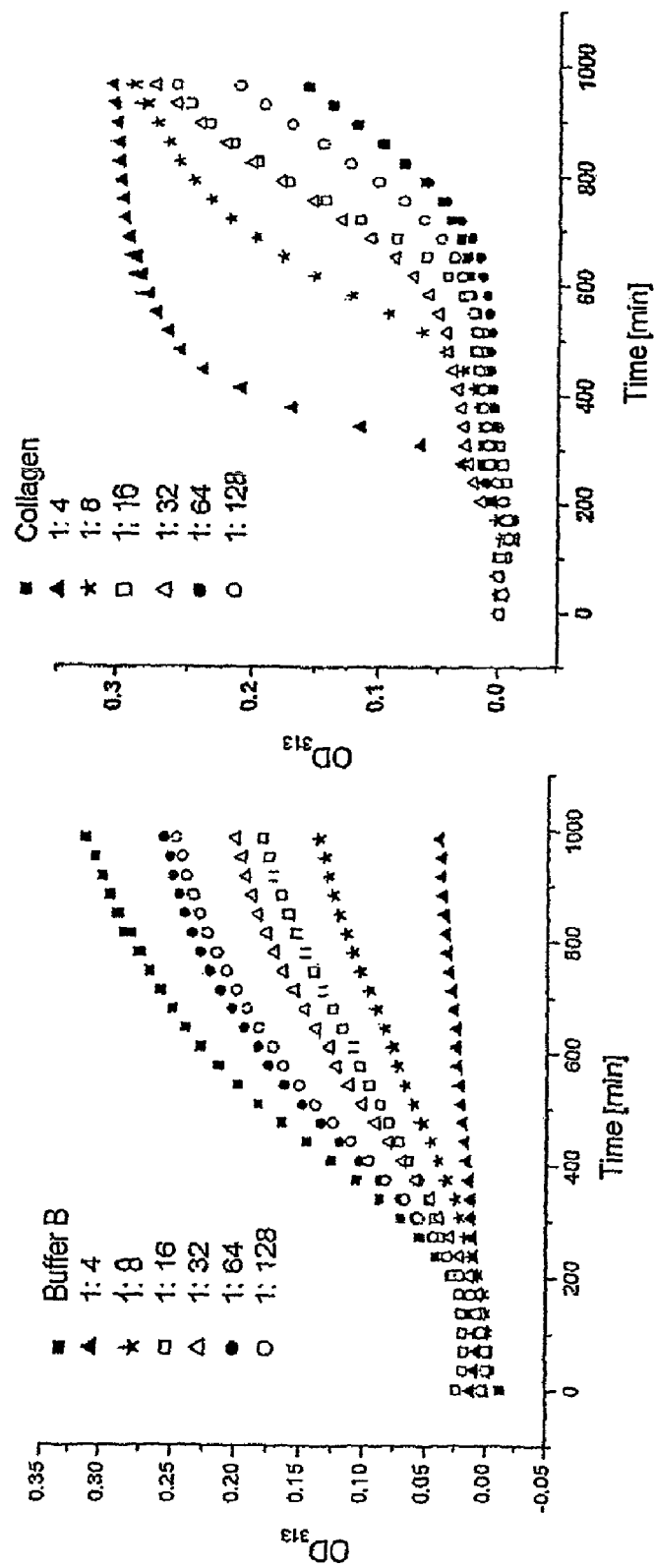
FIG. 1 Influence of decorin and chondroitin sulfate (CS) on the formation of collagen fibrils, measured as the increase in the turbidity of a fibrillogenesis solution in OD over time FIG. 2 AFM photographs of the fibril structure FIG. 3. Chondroitin sulfate and decorin present in osteogenic matrix composites according to the invention FIG. 4 Binding behavior of osteogenic matrix composites according to the invention for the recombinant growth factors BMP-4 and TGF-1β

FIG. 1 shows, in a measurement of the turbidity of a solution caused by fibril formation, over time, that increasing amounts of decorin (indicated in molar ratios) cause a slowing of the formation kinetics and a reduction of the maximum OD values, indicative of a reduction of the fibril diameter. For chondroitin sulfate, an opposite effect is to be observed. Formation conditions: 250 µg/ml of collagen, 37° C., mmol/l of phosphate buffer pH 7.4 containing 135 mmol/l of NaCl.

Figure 2:
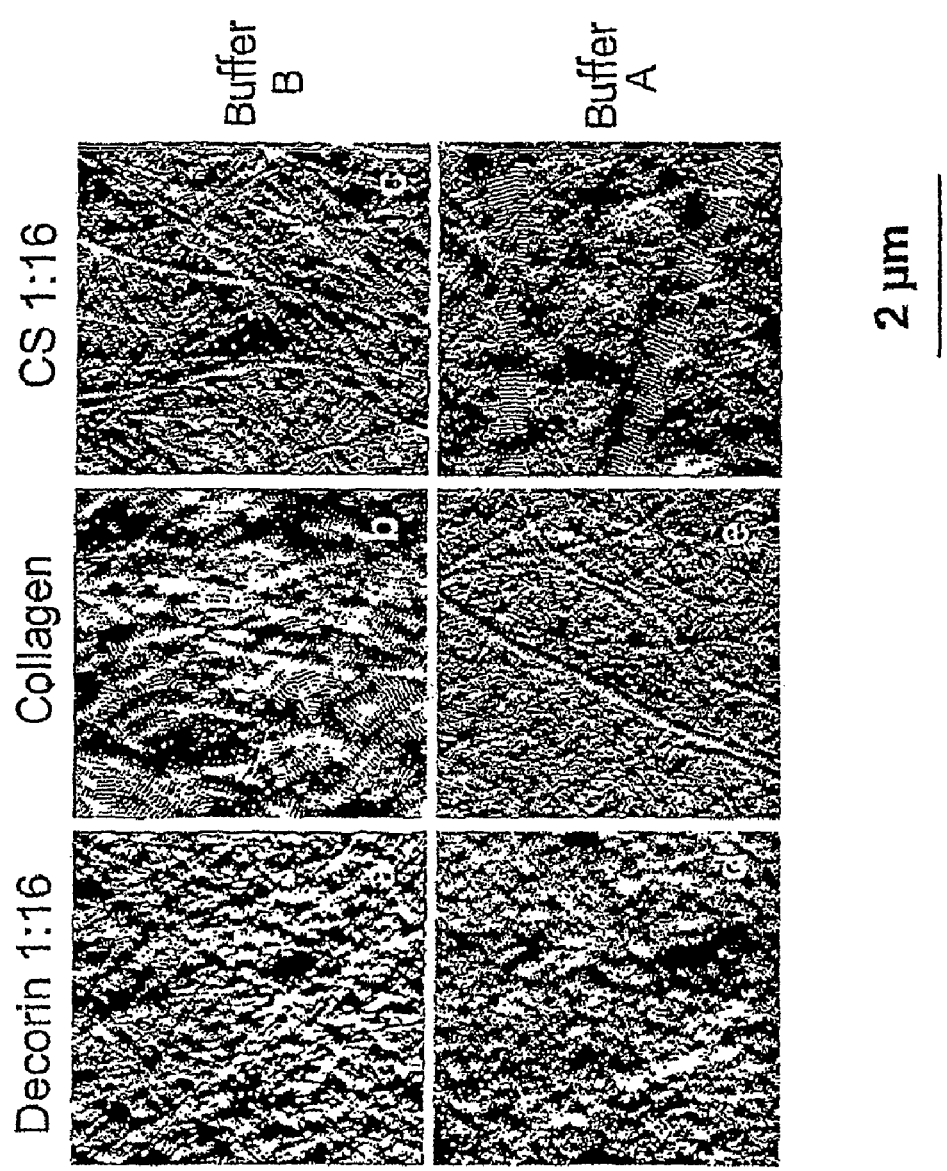

In FIG. 2, the influence of the formation conditions on the structure of the resulting fibrils is documented in AFM photographs. Addition of decorin reduces the fibril diameter (a and d) under all conditions. For chondroitin sulfate, in particular under conditions of low ionic strength, a markedly more heterogeneous distribution of the fibril diameter is visible with increase in the average fibril diameter (f), while the effect is not apparent at higher ionic strengths (c). b and e show the fibril structure without noncollagenic additives. Formation conditions: 250 µg/ml of collagen, 37° C., 30 mmol./l of phosphate buffer pH 7.4 (buffer A) or 30 mmol/l of phosphate buffer pH 7.4 containing 135 mmol/l of NaCl (buffer B).

In all cases, however, during fibrillogenesis in vitro the collagen monomers form the characteristic transversely striated fibrils analogously to the in vivo structures, the structure of the resulting fibrils being influenced both by the process parameters (pH, ionic strength, phosphate concentration) and by the nature and amount of the added noncollagenic components. Collagen fibrils containing noncollagenic constituents such as glycosaminoglycans or decorin can accordingly be produced in a comparatively wide range of mass ratios, within which the integration of the collagen into the fibrils is not or is only slightly influenced.

Working Example 2

Incorporation of Noncollagenic Components Into Collagen Fibrils

For generation of the osteogenic matrix composite, a solution of collagen monomers in 0.01 M acetic acid is prepared by stirring at 4° C. for 24 hours. The collagen fibrils are subsequently formed by a process of self-aggregation (fibrillogenesis) in aqueous phosphate buffer solutions at neutral pH in the presence of the noncollagenic components. Formation conditions: 250 µg/ml of collagen, 37° C., 30 mmol/l of phosphate buffer pH 7.4 (buffer A) or 30 mmol/l of phosphate buffer pH 7.4 containing 135 mmol/l of NaCl (buffer B) with different chondroitin sulfate and decorin concentrations.

After washing and hydrolysis of the fibrils in 500 µl of 6 M HCl at 105° C. for 6 hours, decorin and chondroitin sulfate integrated into the fibrils was determined according to the method of Pieper et al. [Pieper J S, Hafmans T, Veerkamp J H, van Kuppevelt T H. Development of tailor-made collagen-glycosaminoglycan matrices: EDC/NHS crosslinking, and ultrastructural aspects. Biomaterials 2000; 21(6): 581-593].

Figure 3:
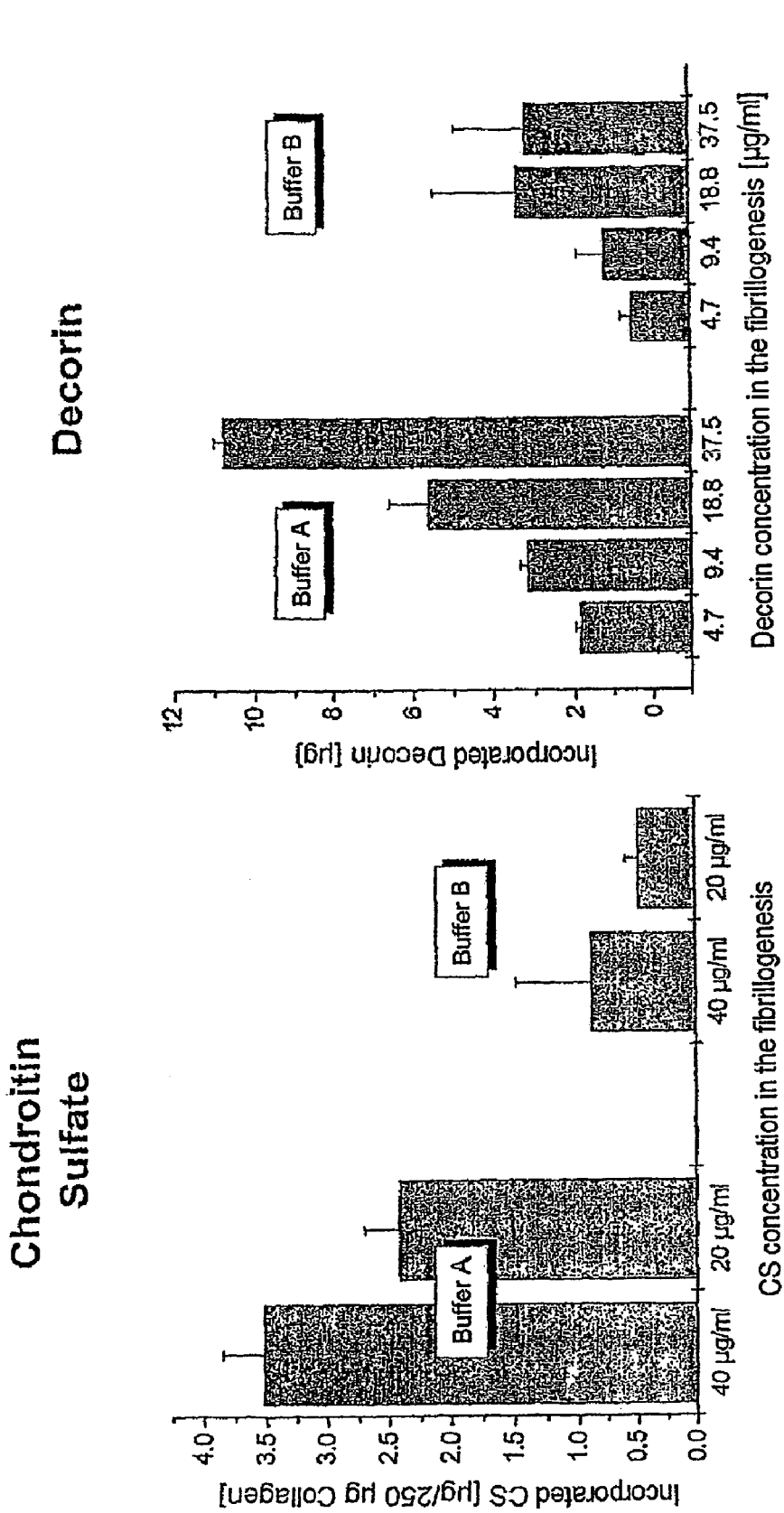

For chondroitin sulfate, the extent of the integration is dependent on the ionic strength of the buffer system used. For low ionic strengths (buffer A); of the 20 µg employed, about 2.5 µg of CS are incorporated on 250 µg of collagen, for high ionic strengths (buffer B), however, only a third of this amount (FIG. 3).

The incorporation of decorin also depends on the buffer system used. For buffer A, a third of the amount employed is incorporated, while the values for buffer B were again markedly lower.

Working Example 3

Recruitment of Growth Factors by an Implant Coated with an Osteogenic Matrix Composite Matrices composed and produced according to the invention can accelerate and improve bone formation and accumulation without the use of recombinant growth factors by the recruitment of endogenous growth factors. In the experiment, such a binding behavior can only be demonstrated using recombinant growth factors.

A sandblasted, cylindrical sample of TiAl6V4 having a diameter of 10 mm is cleaned with ethanol, acetone and water.

A solution of 1 mg/ml of bovine collagen type I in 0.01 M acetic acid is produced by stirring overnight at 4° C. Noncollagenic ECM components (glycosaminoglycan 30 µg/ml, proteoglycans 15 µg/ml) are added to this solution. The mixtures are treated with fibrillogenesis buffer (60 mmol/l of phosphate, 270 mmol/l of NaCl, pH 7.4) on ice and incubated at 37° C. for 18 h. The resulting fibrils are centrifuged off, washed, homogenized and resuspended to give a final concentration of 1 mg/ml.

The cylindrical sample is coated (dip-coating) with this solution at RT for 15 min, washed with water and dried.

Subsequently, growth factors (recombinant BMP-4 or TGF-1β) are immobilized on these surfaces by an adsorption process (4° C., 18 h, from PBS) and subsequently determined by means of ELISA.

Figure 4:
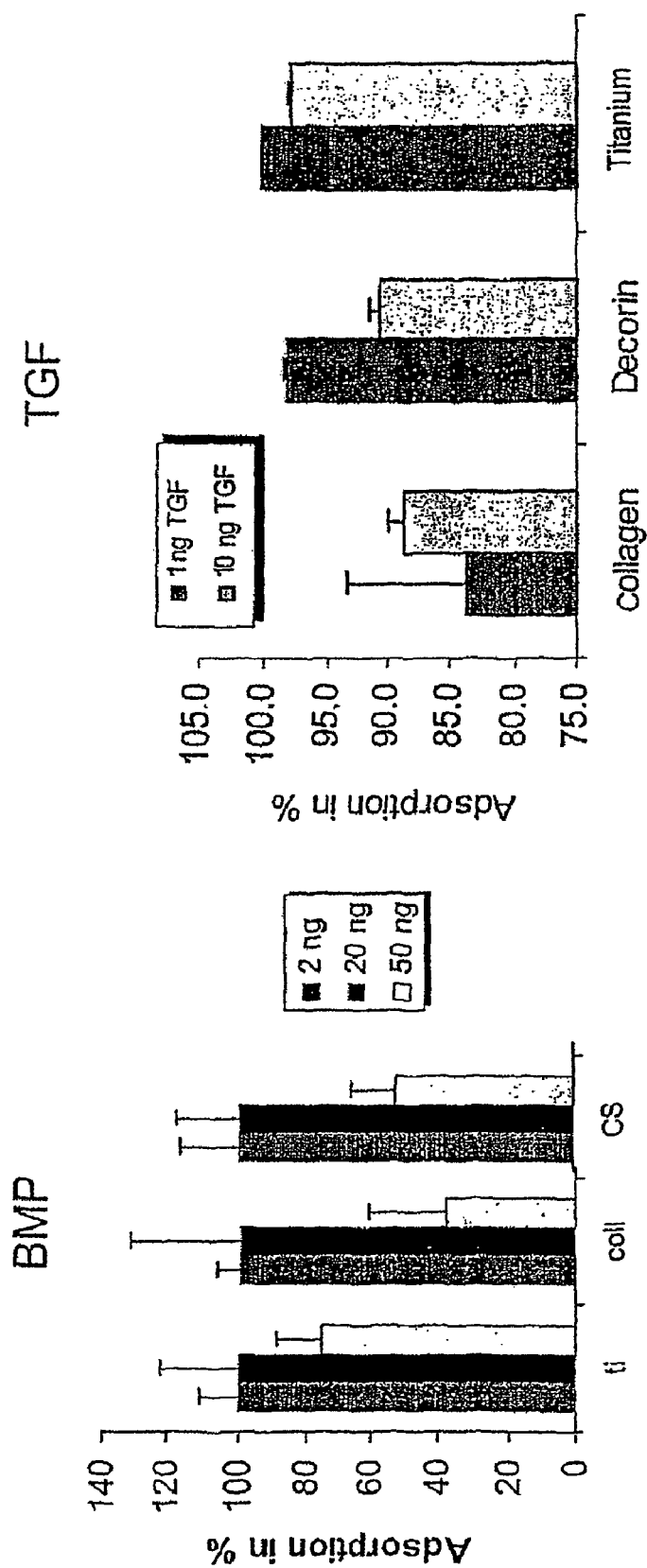

These in vitro tests with recombinant growth factors show that by the addition according to the invention of noncollagenic components, the binding of the growth factors rhBMP-4 (in particular by addition of chondroitin sulfate) or rhTGF-1β (in particular by addition of decorin) to the matrix is increased. For BMP, with small amounts (2-20 ng/cm$^2$) no effect is observed, with higher amounts (from 50 ng/cm$^2$), however, an approximately 10% higher binding to the chondroitin sulfate-containing layer occurs, compared with the pure collagen layer, shown in % of the amount employed (FIG. 4).

For rhTGF-1β, increased binding is detectable on decorin-containing surfaces both for 1 ng/cm$^2$ and for 10 ng/cm$^2$.

Formation conditions of the matrix: 500 µg/ml of collagen, 30 µg/ml of decorin and/or chondroitin sulfate, 37° C., 30 mmol/l of phosphate buffer pH 7.4 containing 135 mmol/l of NaCl.

Working Example 4

Investigations with Rat Calvaria Osteoblasts on Various Matrix Composites

FIG. 5 shows the behavior of primary rat calvaria osteoblasts on various matrices. Initial adhesion of the cells to different matrix compositions was analyzed by means of cell morphology, cytoskeletal organization (actin staining with phalloidin) and formation of the focal adhesion complexes by means of integrin receptors (immunostaining against vinculin). Adhesion was most pronounced after 2 hours on collagen-CS matrices followed by collagen-decorin. The formation of the FACS (green-yellow dots and red on the ends of the actin fibrils) was also promoted and accelerated by decorin and particularly CS. Controls using pure collagen matrices showed significantly less FACS after 2 hours.

The influence of the matrix composition on the differentiation of the osteoblasts was investigated by means of the expression of the marker protein osteopontin by means of fluorescence-activated cell scanning. Osteoblasts on collagen-CS surfaces produced 5 times more osteopontin (~2500 fluorescence units) after 8 days than cells on pure collagen surfaces (~500 fluorescence units). Formation conditions of the matrix: 500 µg/ml of collagen, 30 µg/ml of decorin and/or chondroitin sulfate, 37° C., 30 mmol/l of phosphate buffer pH 7.4 containing 135 mmol/l of NaCl.

Figure 6:
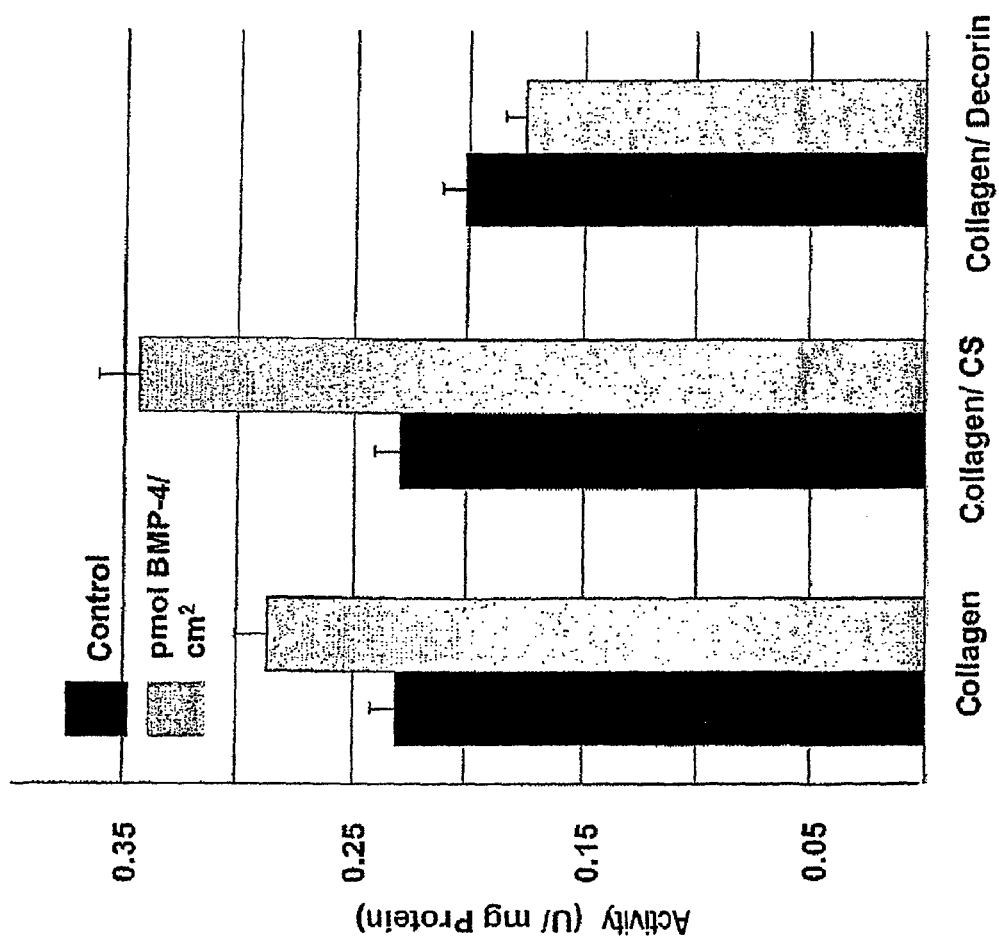

Further investigations with rat calvaria osteoblasts showed different cell reactions on rhBMP-4 depending on the composition of the carrier matrix. FIG. 6 shows the activity of the alkaline phosphatase in activity units U per mg of protein after addition of 4 pmol/cm$^2$ of rhBMP-4 to rat calvaria cells. On decorin-containing matrices, the BMP activity is under-regulated, while on chondroitin sulfate-containing matrices it is increased. Formation conditions of the matrix: 500 µg/ml of collagen; 30 µg/ml of decorin and/or chondroitin sulfate, 37° C., 30 mmol/l of phosphate buffer pH 7.4 containing 135 mmol/l of NaCl.

Working Example 5

Animal Experiments

In animal experiments, it was surprisingly found that matrices provided with recombinant growth factors perform markedly more poorly with respect to induced bone formation than the noncrosslinked osteogenic matrix composites according to the invention based on collagen type I and chondroitin sulfate.

Ti implants, which have annular incisions at right angles to the axis and thus represent a defect model, are cleaned with 1% Triton X-100, acetone and 96% ethanol, rinsed with distilled water and dried.

The implants employed are coated in two successive dip-coating steps with:
A. fibrils of collagen type I,
B. osteogenic matrix composite according to the invention based on collagen type I and chondroitin sulfate according to working example 1
C. osteogenic matrix composite according to the invention based on collagen type I and chondroitin sulfate according to working example 1

The implants are washed with distilled water, air-dried and sterilized with ethylene oxide at 42° C. for 12 h. Immediately before implantation, the surface condition C is coated overnight with recombinant BMP-4. (400 ng/ml) at 4° C. and subsequently dried.

The implants are employed in the lower jaw of minipigs. The bone implant contact was determined histomorphometrically after 6 months.

Figure 7:
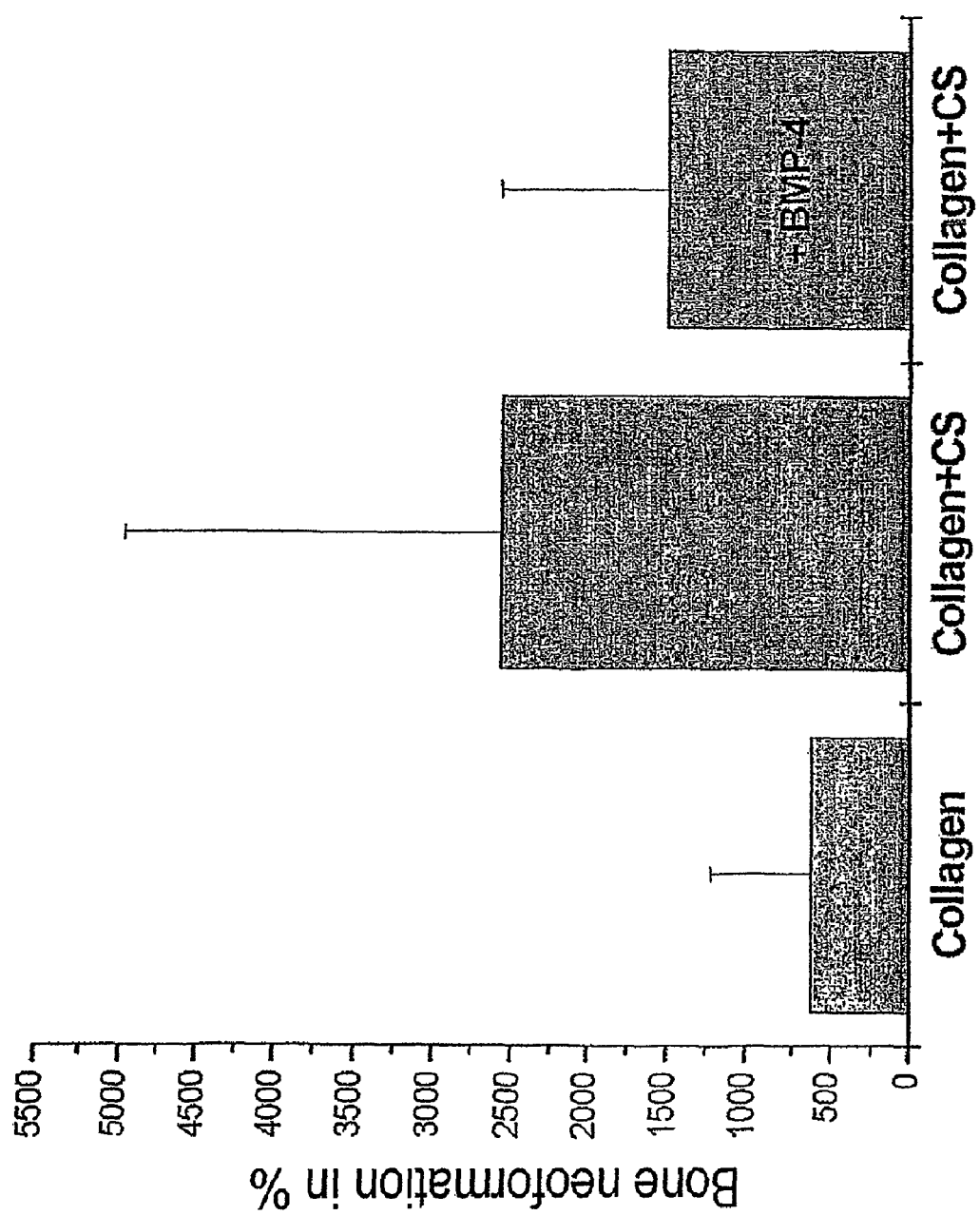
FIG. 7 New bone formation on the implant surface in percent after 6 months in minipig jaw

The highest percentage for this contact is obtained for implants coated with the osteogenic matrix according to the invention based on collagen and chondroitin sulfate (27.8%), while implants with the same coating and recombinant BMP-4 and the combination were around 15% and thus markedly lower. The lowest values are obtained for the pure collagen coating (12.8%) (FIG. 7).

The following abbreviations are used in the description of the invention:
bFGF Basic fibroblast growth factor
BMP Bone morphogenetic protein
ECM Extracellular matrix
EGF Endothelial growth factor
FACITs Fibril associated collagen with interrupted triple helix
FACS Focal adhesion contacts
FGF Fibroblast growth factor
GAG Glycosaminoglycan
HAP Hydroxylapatite
IGF-I Insuline-like growth factor
PGA Polyglycolic acid
PLA Polylactic acid
SLRP Small leucine-rich protein
TCP Tricalcium phosphate phases
TES (N-[Tris(hydroxymethyl)methyl]-2-amino-ethane-sulfonic acid)-
TGF-β Transforming growth factor β
VEGF Vascular endothelial growth factor
WF Growth factor

What is claimed is:

1. A method for the production of an implant or of a scaffold for tissue engineering having a coating of an osteogenic matrix composite, wherein the osteogenic matrix composite is a composite of collagen and at least one non-collagenic extracellular matrix (ECM) component, comprising the steps of:
producing non-crosslinked collagen fibrils by means of fibrillogenesis after integrating the at least one non-collagenic ECM component to the collagen component by adding the at least one non-collagenic ECM component,
re-suspending in water or in a buffer the collagen fibrils thus produced, and
subsequently immobilizing the collagen fibrils on the surface of the implant or the scaffold in a dip-coating process, wherein the collagen fibrils are formed by a process of self-aggregation of collagen monomers.

2. The method for the production of an implant or of a scaffold for tissue engineering as claimed in claim 1, wherein the noncollagenic ECM components contain glycosaminoglycans.

3. The method for the production of an implant or of a scaffold for tissue engineering as claimed in claim 2, wherein the noncollagenic ECM component contains chondroitin sulfate of type A, C, D, or E, dermatan sulfate, keratan sulfate, heparan sulfate, heparin, and/or hyaluronic acid, individually or mixed.

4. The method for the production of an implant or of a scaffold for tissue engineering as claimed in claim 1, wherein the noncollagenic ECM component contains noncollagenic matrix proteins.

5. The method for the production of an implant or of a scaffold for tissue engineering as claimed in claim 4, wherein the noncollagenic ECM component contains, as noncollagenic matrix proteins, fibronectin, decorin, biglycan, laminin, and/or versican, individually or mixed.

6. The method for the production of an implant or of a scaffold for tissue engineering as claimed in claim 1, wherein the collagen component consists of one of the collagens I, II, III, V, IX, XI, or combinations thereof.

7. The method for the production of an implant or of a scaffold for tissue engineering as claimed in claim 1, wherein the osteogenic matrix composite is a composite of type I collagen and at least one selected from the group consisting of chondroitin sulphate and decorin.

8. The method for the production of an implant or of a scaffold for tissue engineering as claimed in claim 1, wherein the fibrillogenesis is carried out under the following conditions: temperature range of 25° C. to 37° C., and/or collagen concentration of 250 to 1000 μg/ml, and/or pH 6 to pH 8, and/or phosphate content of 30 to 60 mmol/l, and/or NaCl content of up to 300 mmol/l.

9. The method for the production of an implant or of a scaffold for tissue engineering as claimed in claim 1, wherein the at least one non-collagenic ECM component is integrated into the non-crosslinked collagen fibrils.

10. A method for the production of a scaffold for tissue engineering having a coating of an osteogenic matrix composite, wherein the osteogenic matrix composite is a composite of collagen and at least one non-collagenic ECM component, comprising the steps of:
producing non-crosslinked collagen fibrils by means of fibrillogenesis after integrating the at least one non-collagenic ECM component to the collagen component by adding the at least one non-collagenic ECM component to the collagen component in such a way that fibril formation is induced in the scaffold, where the fibrils formed in situ either remain as a gel or are dried, and wherein the collagen fibrils are formed by a process of self-aggregation of collagen monomers.

11. The method for the production of an implant or of a scaffold for tissue engineering as claimed in claim 10, wherein the noncollagenic ECM components contain glycosaminoglycans.

12. The method for the production of an implant or of a scaffold for tissue engineering as claimed in claim 11, wherein the noncollagenic ECM component contains chondroitin sulfate of type A, C, D, or E, dermatan sulfate, keratan sulfate, heparan sulfate, heparin, and/or hyaluronic acid, individually or mixed.

13. The method for the production of an implant or of a scaffold for tissue engineering as claimed in claim 10, wherein the noncollagenic ECM component contains noncollagenic matrix proteins.

14. The method for the production of an implant or of a scaffold for tissue engineering as claimed in claim 13, wherein the noncollagenic ECM component contains, as noncollagenic matrix proteins, fibronectin, decorin, biglycan, laminin, and/or versican, individually or mixed.

15. The method for the production of an implant or of a scaffold for tissue engineering as claimed in claim 10, wherein the collagen component consists of one of the collagens I, II, III, V, IX, XI, or combinations thereof.

16. A method for the production of an implant or of a scaffold for tissue engineering having a coating of an osteogenic matrix composite, wherein the osteogenic matrix composite is a composite of collagen and at least one non-collagenic ECM component, comprising the steps of:
producing non-crosslinked collagen fibrils by means of fibrillogenesis after integrating the at least one non-collagenic ECM component to the collagen component by adding the at least one non-collagenic ECM component, re-suspending in water or in a buffer the collagen fibrils thus produced and subsequently immobilizing the collagen fibrils on the surface of the implant or the scaffold in a dip-coating process, wherein the collagen fibrils are formed by a process of self-aggregation of collagen monomers, and wherein fibril formation is induced by the pH, the temperature, and the ionic strength of a cold, acidic collagen solution being brought to values in the vicinity of the physiological parameters.

17. A method for the production of an implant or of a scaffold for tissue engineering having a coating of an osteogenic matrix composite, wherein the osteogenic matrix composite is a composite of collagen and at least one non-collagenic ECM component, comprising the steps of:
producing non-crosslinked collagen fibrils by means of fibrillogenesis after integrating the at least one non-collagenic ECM component to the collagen component by adding the at least one non-collagenic ECM component, re-suspending in water or in a buffer the collagen fibrils thus produced and subsequently immobilizing the collagen fibrils on the surface of the implant or the scaffold in a dip-coating process, wherein the collagen fibrils are formed by a process of self-aggregation of collagen monomers, and wherein the fibrillogenesis is carried out under the following conditions: temperature range from 4° C. to 40° C., collagen concentration of 50 to 5000 μg/ml, pH 4 to pH 9, phosphate content up to 500 mmol/l, NaCl content up to 1000 mmol/l.

* * * * *